(12) United States Patent
Damit et al.

(10) Patent No.: US 9,078,940 B2
(45) Date of Patent: Jul. 14, 2015

(54) INFRARED RADIATION FILTER SYSTEMS, METHODS OF USE AND METHODS OF DISINFECTION AND DECONTAMINATION

(71) Applicant: University of Florida Research Foundation, Inc., Gainesville, FL (US)

(72) Inventors: Brian Eduardo Damit, Silver Spring, MD (US); Chang-Yu Wu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/597,299

(22) Filed: Jan. 15, 2015

(65) Prior Publication Data
US 2015/0157757 A1    Jun. 11, 2015

Related U.S. Application Data

(62) Division of application No. 13/583,977, filed as application No. PCT/US2011/029303 on Mar. 22, 2011, now Pat. No. 8,963,109.

(60) Provisional application No. 61/316,077, filed on Mar. 22, 2010.

(51) Int. Cl.
*A61L 2/00* (2006.01)
*A61L 9/18* (2006.01)

(52) U.S. Cl.
CPC ........................ *A61L 9/18* (2013.01)

(58) Field of Classification Search
USPC ...................................... 250/504 R
See application file for complete search history.

(56) References Cited

U.S. PATENT DOCUMENTS

| | | | |
|---|---|---|---|
| 3,923,038 A | 12/1975 | Cutchaw | |
| 4,067,315 A | 1/1978 | Fehlner et al. | |
| 4,180,055 A | 12/1979 | Hudnall | |
| 4,659,906 A | 4/1987 | Furtek | |
| 5,034,235 A | 7/1991 | Dunn et al. | |
| 5,039,535 A | 8/1991 | Lang et al. | |
| 5,039,865 A * | 8/1991 | Koji ........................ | 250/455.11 |
| 5,394,934 A | 3/1995 | Rein et al. | |
| 5,472,720 A | 12/1995 | Rakhimov et al. | |
| 5,601,786 A | 2/1997 | Monagan | |
| 5,635,059 A * | 6/1997 | Johnson ........................ | 210/192 |
| 5,656,242 A | 8/1997 | Morrow et al. | |
| 7,507,369 B2 * | 3/2009 | Lu .................................. | 422/22 |

(Continued)

FOREIGN PATENT DOCUMENTS

| | | |
|---|---|---|
| WO | 2008000317 | 1/2008 |
| WO | 2008006681 | 1/2008 |
| WO | 2008154503 | 12/2008 |

OTHER PUBLICATIONS

The International Preliminary Report on Patentability dated Sep. 25, 2012.

(Continued)

*Primary Examiner* — Phillip A Johnston
(74) *Attorney, Agent, or Firm* — Thomas Horstemeyer, LLP

(57) ABSTRACT

In accordance with the purpose(s) of the present disclosure, as embodied and broadly described herein, embodiments of the present disclosure, in one aspect, relate to infrared (IR) filter systems, methods of using the IR filter systems, and methods of degrading a contaminant, and the like.

7 Claims, 5 Drawing Sheets

(56) References Cited

U.S. PATENT DOCUMENTS

2004/0173092 A1 9/2004 Moore et al.
2009/0196794 A1 8/2009 Smith et al.

OTHER PUBLICATIONS

Abstract of "Potential of Infrared Heating as a Method for Decontaminating Food Powder Process Development and Impact on Product Quality".

Sawai, et al., "Characteristics of the Inactivation of *Escherichia coli* by Infrared Irradiative Heating," Biocontrol Sci Jun. 2006;11(2):85-90.

Abstract of McDonnell, "Antisepsis, Disinfection, and Sterilization: Types, Action and Resistance" 2007, p. 65.

Mata Portuguez, et al., "Sterilization of Heat-Resistant Instrucments with Infrared Radiation," Infect Control Hosp Epidemiol 2002;23:393-396.

Allen, "*Mycobacterium szulgai*; Malnutrition and Wounds: Biological Indicators: Sterilizing with Infrared Radiation," AORN Journal, Nov. 1, 2022.

* cited by examiner

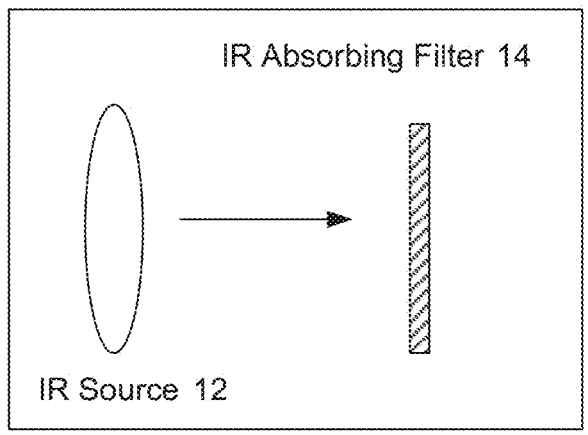
FIG. 1.1A
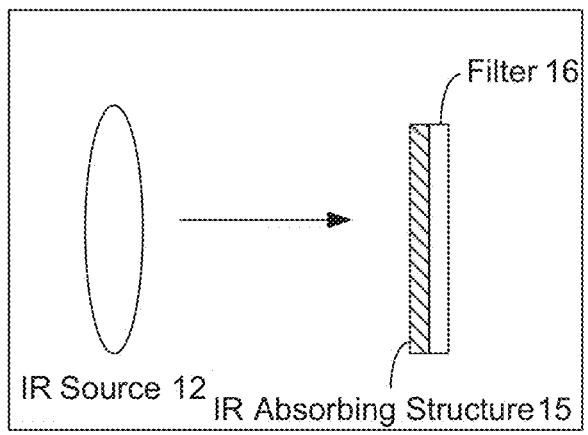
FIG. 1.1B
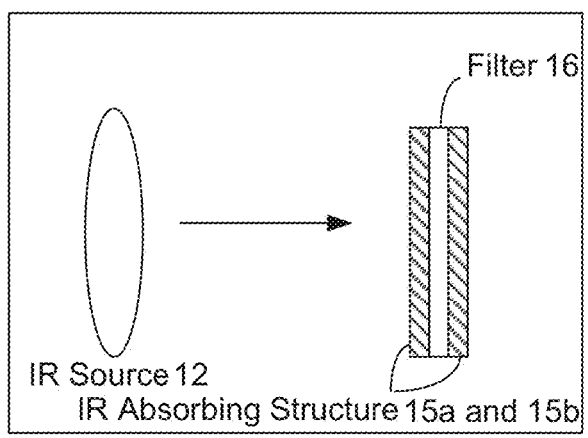
FIG. 1.1C

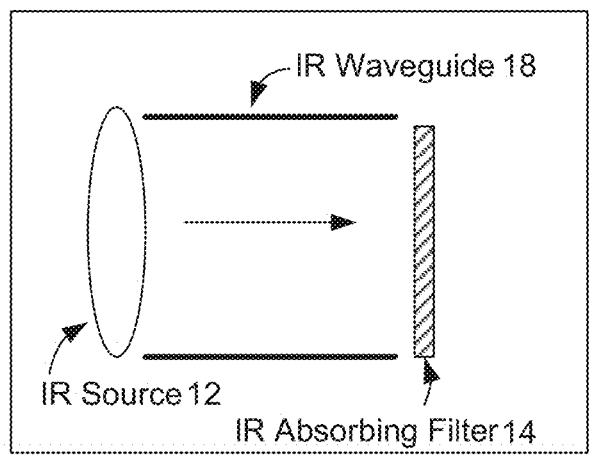
FIG. 1.1D
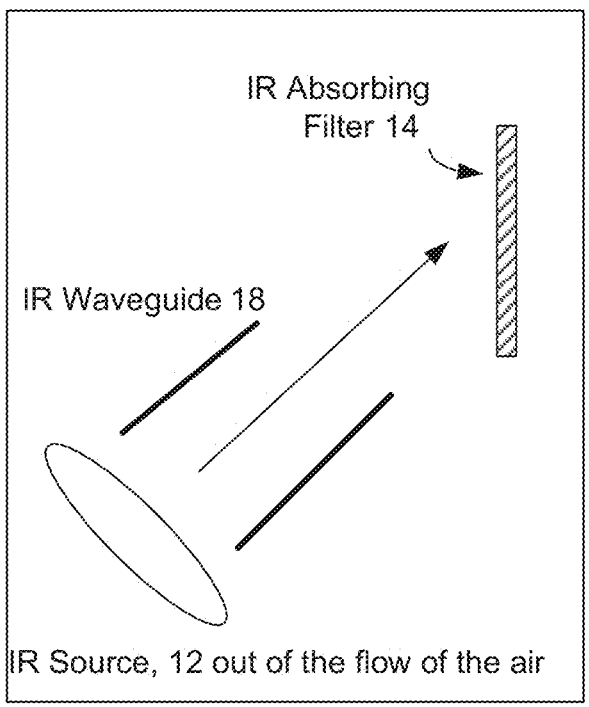
FIG. 1.1E

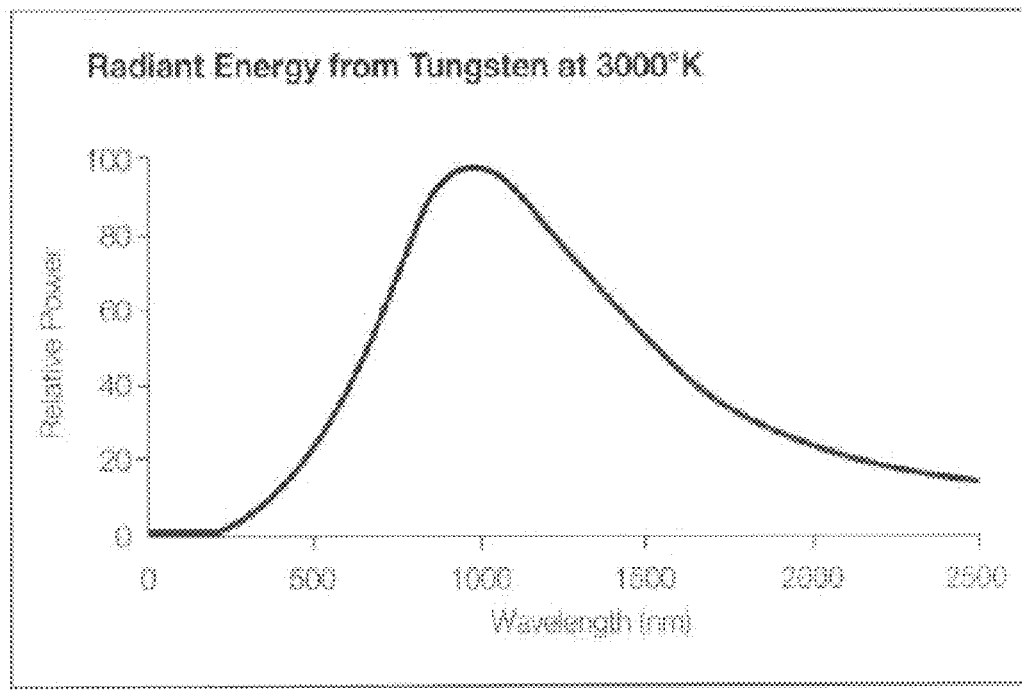
FIG. 2.1
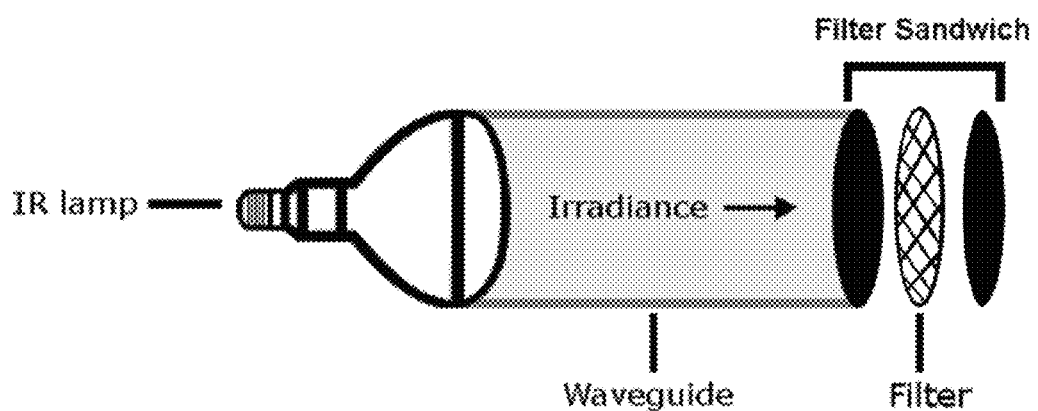
FIG. 2.2

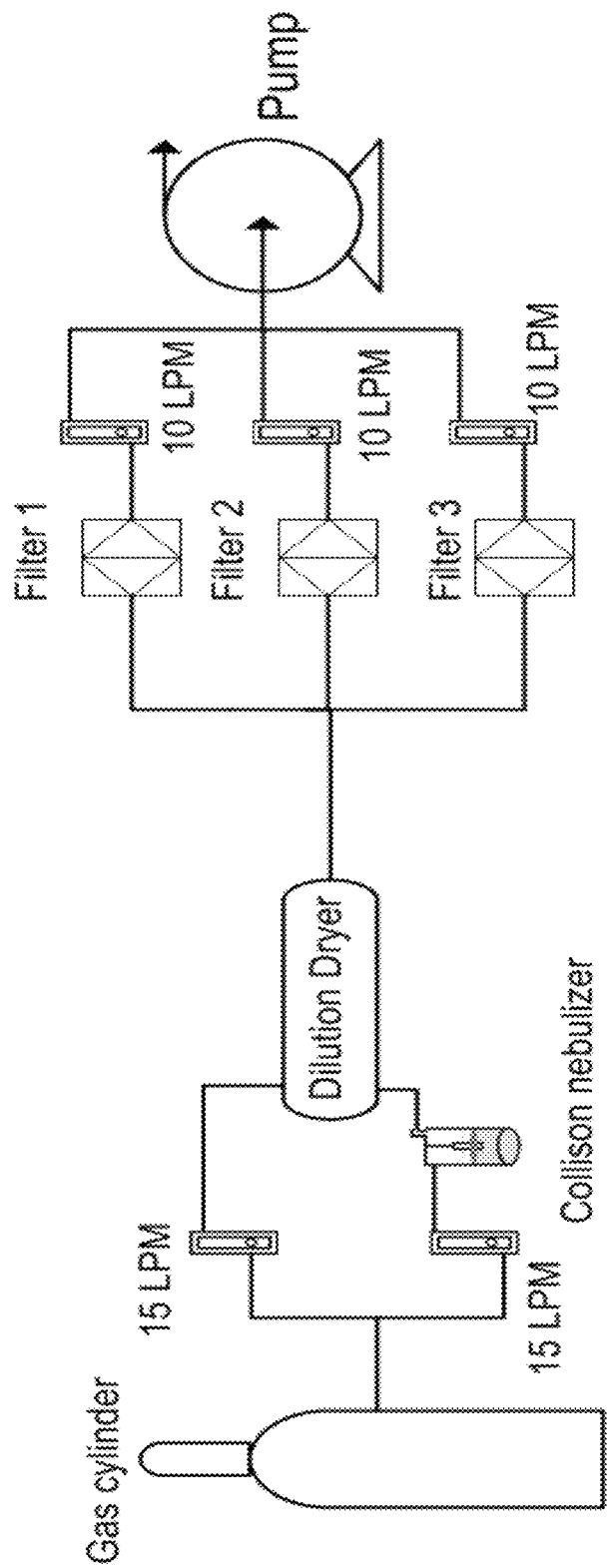
FIG. 2.3

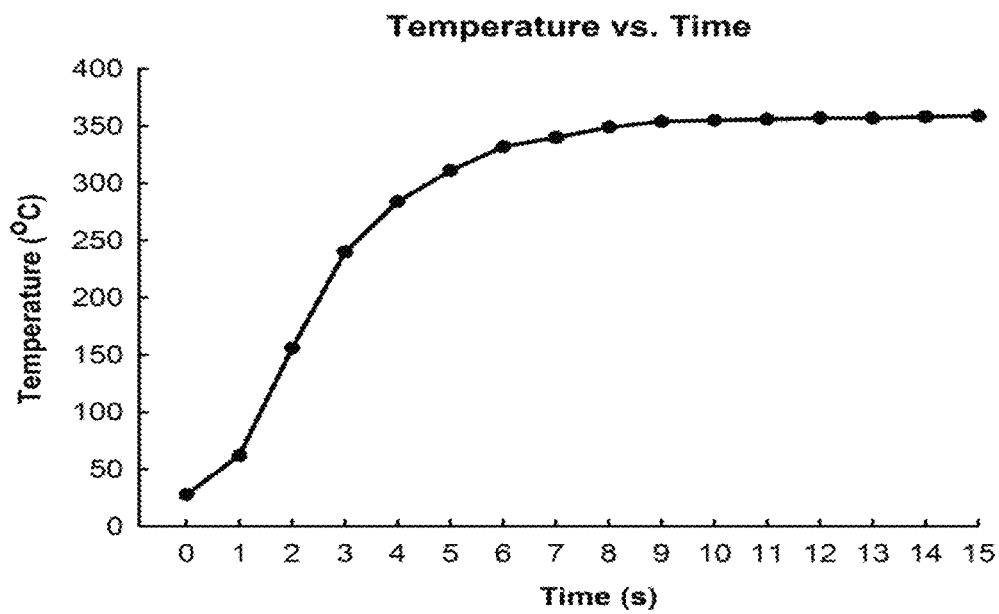
FIG. 2.4
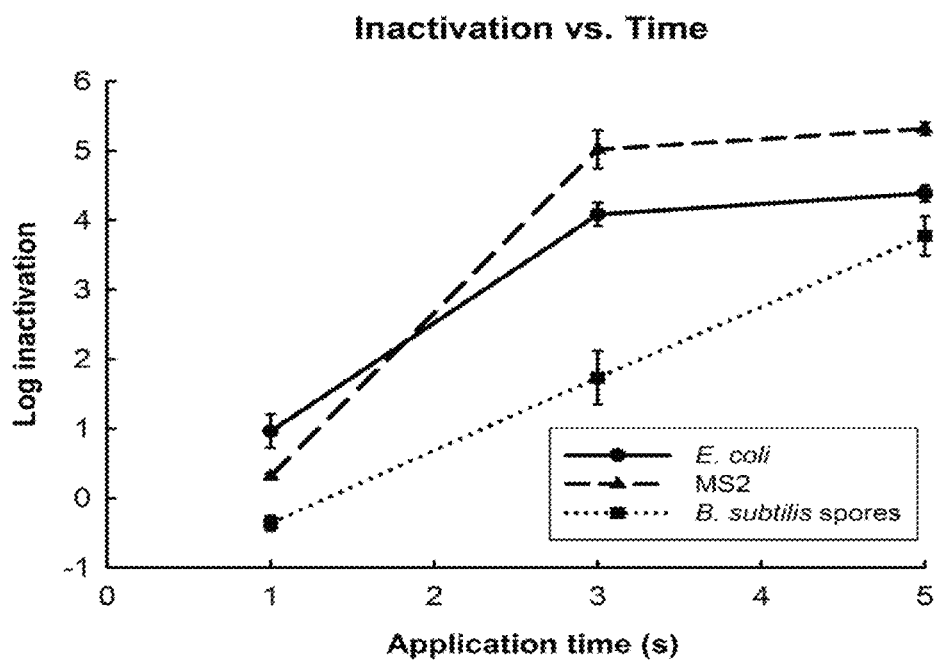
FIG. 2.5

INFRARED RADIATION FILTER SYSTEMS, METHODS OF USE AND METHODS OF DISINFECTION AND DECONTAMINATION

CROSS-REFERENCE TO RELATED APPLICATION

This application is a divisional and claims priority to U.S. Non-Provisional Patent Application entitled: "INFRARED RADIATION FILTER SYSTEMS, METHODS OF USE, AND METHODS OF DISINFECTION AND DECONTAMINATION, which is the 35 U.S.C. §371 national stage of PCT application PCT/US2011/29303, filed Mar. 22, 2011, which claims priority to and the benefit of U.S. provisional application entitled "INFRARED RADIATION FILTER SYSTEMS, METHODS OF USE, AND METHODS OF DISINFECTION AND DECONTAMINATION" having Ser. No. 61/316,077, filed Mar. 22, 2010, both of which are hereby incorporated by reference in their entirety.

BACKGROUND

The disinfection of airborne pathogens has been given more attention due to the 2009 H1N1 swine flu pandemic and the increasing threat of bioterrorism. Pathogenic bioaerosols are a danger to humans and can be generated from a variety of sources; bioterrorism, occupational and agricultural processes, even coughing and sneezing aerosolize pathogens which can remain suspended and infectious for days. While there are a number of current bioaerosol control technologies including Ultraviolet Germicidal Irradiation (UVGI), antimicrobial filters, and photocatalytic oxidation, they have some noticeable weaknesses. The current technologies not only suffer from being expensive to install and maintain, but also are ineffective against highly resistant bacterial endospores (e.g., anthrax spores).

Filtration is the most commonly used method for the removal of particles, viable and nonviable alike. For example, Heating, Ventilating and Air Conditioning (HVAC) filters are widely used in buildings to provide filtered breathing air to occupants. Nevertheless, sustained viability of microorganisms collected on the filters, their growth and reaerosolization are major concerns. In addition to HVAC filters, personal respiratory filters loaded with pathogens also present a health and safety concern. In case of pandemic, the lack of personal respiratory filters may require contaminated filters to be reused. Therefore, it is critically important to effectively inactivate pathogens collected on a variety of fibrous filter media.

SUMMARY

In accordance with the purpose(s) of the present disclosure, as embodied and broadly described herein, embodiments of the present disclosure, in one aspect, relate to infrared (IR) filter systems, methods of using the IR filter systems, and methods of degrading a contaminant, and the like.

An embodiment of the present disclosure provides for an IR filter system that includes: an IR source; and an IR absorbing filter, where the IR source is positioned relative to the IR absorbing filter so that the IR radiation from the IR source is directed onto the IR absorbing filter to cause the IR absorbing filter to increase in temperature to about 135° C. or greater.

An embodiment of the present disclosure provides for a method of degrading contaminates that includes: providing an IR filter system as described herein; trapping contaminants in the IR absorbing filter; irradiating the IR absorbing filter with IR radiation, wherein the IR absorbing filter absorbs IR radiation causing the IR absorbing filter to increase in temperature to about 135° C. or greater; and degrading the contaminants trapped in the IR absorbing filter.

An embodiment of the present disclosure provides for an IR filter system that includes: an IR source; a filter; an IR absorbing structure, wherein the filter and the IR absorbing structure are disposed in a plane parallel each other, wherein the filter and the IR absorbing structure are in contact with each other along one side, wherein the IR source is positioned relative to the IR absorbing structure and filter so that the IR radiation from the IR source is directed onto the IR absorbing structure to cause the IR absorbing structure and filter to increase in temperature to about 135° C. or greater.

An embodiment of the present disclosure provides for a method of degrading contaminates that includes: providing an IR filter system as described herein; trapping contaminants in the filter; irradiating the IR absorbing structure with the IR radiation source, wherein the IR absorbing structure absorbs IR radiation causing the IR absorbing structure to increase in temperature to about 135° C. or greater, wherein the filter increases in temperature since it is in contact with the IR absorbing structure; and degrading the contaminants trapped in the filter.

An embodiment of the present disclosure provides for an air filtration system that includes an IR filter system as described herein.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIGS. 1.1A-1.1E illustrate embodiments of IR filter system.

FIG. 2.1 illustrates a wavelength spectrum of emitted IR radiation.

FIG. 2.2 illustrates a schematic of the IR disinfection device.

FIG. 2.3 illustrates a diagram of the bioaerosol loading system.

FIG. 2.4 illustrates the filter temperature as a function of time due to irradiation by a 250-W bulb.

FIG. 2.5 illustrates the inactivation curves when a 250-W bulb was employed in the device.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of environmental engineering, biology, molecular biology, chemistry, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

The terms "bacteria" or "bacterium" include, but are not limited to, Gram-positive and Gram-negative bacteria and endospores of these.

The term "protozoan" as used herein includes the following as well as cysts of the following: flagellates (e.g., *Giardia lamblia*), amoeboids (e.g., *Entamoeba histolitica*), sporozoans (e.g., *Plasmodium knowlesi*), and ciliates (e.g., *B. coli*).

The term "algae" as used herein includes the following as well as spores of any of the following: microalgae and filamentous algae.

The term "fungi" as used herein includes the following as well as spores of any of the following: molds, mildews and rusts.

The term "degrade", "degrading", or "degradation" refers, but is not limited to, the degradation of the contaminant so that it is not harmful, the conversion of the contaminant into another compound that is either less toxic or nontoxic, and/or the destruction of the contaminant into a carbonized material, by embodiments of the present disclosure. The phrases "degrade substantially all", "degrading substantially all", or the like can refer to degrading greater than about 70%, about 80%, about 90%, about 95%, about 99%, about 99.9%, about 99.99%, of the contaminate. In an embodiment a contaminate can include a specifically targeted contaminate or more than one specifically targeted contaminate, but may not include all contaminates.

DISCUSSION

In accordance with the purpose(s) of the present disclosure, as embodied and broadly described herein, embodiments of the present disclosure, in one aspect, relate to infrared (IR) filter systems, methods of using the IR filter systems, and methods of degrading a contaminant, and the like.

Embodiments of the present disclosure are able to degrade a contaminant on a filter surface by heating the filter, directly or indirectly, using IR radiation. Compared to other radiation (e.g., microwave, UV, X-ray, etc.) IR has ideal characteristics to be implemented in a filter regeneration process as it is effective, safe, inexpensive and easily generated. It should be noted that other radiation does not have the ability to rapidly and uniformly supply the thermal energy required as does IR radiation.

In an embodiment, the filter can increase in temperature from about room temperature (25° C.) (or another temperature depending on the circumstances) to 135° C. or greater (e.g., about 250° C. or more, or about 350° C. or more) in a matter of seconds (e.g., about 5 seconds or less in some instances). The contaminant can be a biological contaminant (e.g., a spore) and/or a chemical contaminant (e.g., volatile organic compound). Embodiments of the present disclosure can target one or more contaminants and can degrade all or a substantial portion of the targeted contaminant(s). In an embodiment, heat resistant bacterial endospores (*Bacillus subtilis*), which are more difficult to degrade than many other biological contaminants, on a filter were degraded at greater than 99.99% in less than 5 seconds. Thus, embodiments of the present disclosure can quickly and uniformly degrade contaminants on a filter in a short period of time (e.g., seconds) without releasing contaminants (e.g., purify the air that flows through the filter system).

Embodiments of the present disclosure can be used in HVAC systems, portable filter systems, respirator systems, and other air circulation or air control systems. Additional details are provided below and in the Example section.

In an embodiment, the IR filter system includes an IR source and an IR absorbing filter. The IR source produces IR radiation. In an embodiment, the wavelength of the IR radiation can be selected to specifically degrade selected contaminants. In an embodiment, the IR filter system can include two or more IR sources that can be used to produce different wavelengths of IR radiation. In an embodiment, the IR source is positioned in-line with the IR absorbing filter so that the IR radiation uniformly contacts the IR absorbing filter. In other embodiments, one or more IR sources can be positioned on one or both sides of the IR absorbing filter and/or at one or more angles relative to the IR absorbing filter. In an embodiment, one or more IR sources are positioned so that the IR absorbing filter is substantially uniformly contacted by IR radiation. In an embodiment, an IR waveguide can be used to direct the IR from the source to reach the target filter. In another embodiment, an IR reflector can be used to direct the IR radiation onto the IR absorbing filter. In any one of the embodiments described herein, the IR source can be turned on for short periods of time (e.g., seconds or minutes) or can be on for longer periods of time (e.g., hours or days). In an embodiment the IR source can be regularly (e.g., every few seconds) turned on and off so that the IR absorbing filter maintains a temperature (or temperature range) for a period of time. In an embodiment, the IR source can be an IR heat lamp, laser, sunlight, or any IR producing heated filament. The time that the IR source is on, the number of IR sources, the relative position of the IR source(s) to the IR absorbing filter, and/or the relative position of the IR source(s) in the IR filter system, depends, at least in part, upon the intended use of the IR filter system, use of an IR reflector, use of an IR waveguide, the exposure to contaminants, the type of contaminants, and the like.

The IR absorbing filter is adapted to absorb IR radiation. The IR absorbing filter converts the IR radiation into heat so that the IR absorbing filter increases in temperature. In an embodiment, the temperature can increase 100° C. or more in a matter of seconds (e.g., about 3 seconds or more, about 5 seconds or more, about 10 seconds or more, and the like). In an embodiment, the temperature of the IR absorbing filter can increase from about room temperature to 135° C. in about 3 seconds. In another embodiment, the temperature of the IR absorbing filter can increase from about room temperature to about 250° C. in about 5 seconds. In another embodiment, the temperature of the IR absorbing filter can increase from about room temperature to about 350° C. in about 5 seconds. The temperature can be held for a period of time from seconds to minutes to hours. The speed of the temperature increase will depend, at least in part, upon the intended use of the IR filter system, the exposure to contaminants, use of an IR reflector, use of an IR waveguide, the type of contaminants, the IR source and the like. Although the IR absorbing filter can be heated to very high temperatures in a short period of time (e.g., 3 seconds or 5 seconds), it is contemplated that longer time periods may be desired so embodiments of the present disclosure are not intended to be limited to a few seconds or minutes, but could extend to longer periods of time.

The IR absorbing filter can include filters including activated carbon, activated carbon filters, activated carbon fiber mats, or any filter media with high absorption of the IR radiation to be used. The IR absorbing filter can be about 0.1 to 2 mm thick. The length and width of the IR absorbing filter can vary depending on the specific IR filter system. The type (e.g., material, size, and the like) of IR absorbing filter will depend, at least in part, upon the intended use of the IR filter system, the exposure to contaminants, the type of contaminants, and the like.

In an embodiment, the relative position of the IR source and the IR absorbing filter can vary depending upon the IR filter system and/or the system that the IR filter system is incorporated into. For example, the IR source(s) can be in-line with the IR absorbing filter or offset (or at an angle). In an embodiment, the IR filter system can be designed to also be in-line with the air flow through the IR absorbing filter. In another embodiment, the IR source(s) is not in-line with the air flow. The relative position of the IR source(s) and/or the air flow can be designed in a number of ways, where the intent is to have a design so that the contaminant collected on the IR absorbing filter is degraded by the heat generated by the IR absorbing filter absorbing the IR radiation.

In an embodiment, a method includes trapping one or more types of contaminants in the IR absorbing filter. Periodically or continuously, the IR absorbing filter can be irradiated with IR radiation from one or more IR sources. The configuration of the IR sources can be any one of those described herein or within the scope of this disclosure. The IR absorbing filter absorbs IR radiation causing the IR absorbing filter to increase in temperature from about room temperature to about 135° C. or greater. In an embodiment the increase in temperature of the IR absorbing filter can occur within a few seconds (e.g., about 3 or 5 seconds). After a sufficient period of time, one or more types of contaminant trapped in the IR absorbing filter is degraded or substantially degraded. The degree of degradation can depend upon the time that the IR source is on, the temperature of the IR absorbing filter, the time that the filter is held at a high temperature, the type of contaminant, and the like. The use and design can be used to determine the configuration of the IR filter system (e.g., the type of IR absorbing filter, the IR source, the temperature, the time that the temperature is sustained, and the like).

In another embodiment, the IR filter system includes one or more IR sources, a filter, and an IR absorbing structure. The IR source(s) can be any of the IR sources described herein. The IR source(s) can be positioned and/or used in any of the ways described in other embodiments described herein. The IR absorbing structure can be disposed in a plane parallel to the filter so that heat from the IR absorbing structure causes the filter to increase in temperature. In an embodiment, the IR absorbing structure is disposed in a plane parallel to the filter and is in direct physical contact with the filter along one side of the filter (e.g., in contact with most (e.g., about 80%, 90%, 95%, 99%, or more of the side of the filter) if not all of the filter side portion that air passes through). The filter can be a filter that is able to absorb heat from the IR absorbing material. In an embodiment, the filter can be a HEPA, a hyper-HEPA filter, ULPA, commercial HVAC filter, and the like.

In another embodiment, the IR filter system includes two IR absorbing structures. The first IR absorbing structure is positioned on one side of a filter and the second IR absorbing structure is positioned on the other side of the filter (e.g., in contact with most (e.g., about 80%, 90%, 95%, 99%, or more of the side of the filter) if not all of the filter side portion that air passes through). Each of the IR absorbing structures can be disposed in a plane parallel to the filter (each on opposite sides of the filter) so that heat from the IR absorbing structures causes the filter to increase in temperature. In an embodiment, each of the IR absorbing structures is disposed in a plane parallel to the filter and is in direct physical contact with the filter, each along one side of the filter.

The IR absorbing structure absorbs IR radiation from an IR source and increases in temperature much like the IR absorbing filter described above. The IR absorbing structure is not intended to be a filter and the IR absorbing structure does not significantly impede the air flow. However, in an embodiment, the IR absorbing structure is a filter. The IR absorbing structure transmits heat to the filter so that the filter increases in temperature. In an embodiment, the temperature can increase 100° C. or more in a matter of seconds (e.g., about 3 seconds or more, about 5 seconds or more, about 10 seconds or more, and the like). In an embodiment, the temperature can increase from about room temperature to 135° C. in about 3 seconds. In another embodiment, the temperature can increase from about room temperature to about 250° C. in about 5 seconds. In another embodiment, the temperature can increase from about room temperature to about 350° C. in about 5 seconds. The temperature can be held for a period of time from seconds to minutes to hours. The speed of the temperature increase will depend, at least in part, upon the intended use of the IR filter system, the IR absorbing structure(s), the filter, the relative position of the filter and the IR absorbing structure, the exposure to contaminants, the type of contaminants, and the like.

The IR absorbing structure can include structures made of materials such as activated carbon, activated carbon fiber mats, or a filter medium with high absorption of the IR radiation to be used. The IR absorbing structure can be about 0.1 to 2 mm thick. The length and width of the IR absorbing structure can vary depending on the specific IR filter system.

In an embodiment, a method includes trapping one or more types of contaminants in the filter. Periodically or continuously, the IR absorbing structure(s) can be irradiated with IR radiation from one or more IR sources. The configuration of the IR sources can be any one of those described herein or within the scope of this disclosure. The IR absorbing structure absorbs IR radiation causing the IR absorbing structure to increase in temperature from about room temperature to about 135° C. or greater. Since the IR absorbing structure is disposed adjacent (e.g., in a plane parallel and in direct contact) the filter, the filter increases in temperature in a manner similar or exactly the same as the IR absorbing structure. In an embodiment the increase in temperature of the IR absorbing filter can occur with a few seconds (e.g., about 3 or 5 seconds). After a sufficient period of time, one or more types of contaminants trapped in the filter are degraded. The degree of degradation can depend upon the time that the IR source is on, the temperature of the filter, the time that the filter is held at a high temperature, the type of contaminant, and the like. The use and design can be used to determine the configuration of the IR filter system (e.g., the type of IR absorbing structure, filter, the IR source, the temperature, the time that the temperature is sustained, and the like).

Embodiments of the IR filter system are shown in FIGS. 1.1A-1.1E. Other configurations are contemplated to be included herein with various designs of the IR waveguide(s), IR reflector(s), and the like.

FIG. 1.1A illustrates an embodiment of an IR filter system 10a that includes an IR source 12 in-line with an IR absorbing filter 14. The IR source and the IR absorbing filter can include any of those described herein.

FIG. 1.1B illustrates an embodiment of an IR filter system 10b that includes an IR source 12 in-line with an IR absorbing structure 15 and filter 16. The IR source, the IR absorbing structure, and the filter can include any of those described herein.

FIG. 1.1C illustrates an embodiment of an IR filter system 10c that includes an IR source 12 in-line with a IR absorbing structure 15a/filter 16/IR absorbing structure 15b. The IR source, the IR absorbing structures, and the filter can include any of those described herein.

FIG. 1.1D illustrates an embodiment of an IR filter system 10d that includes an IR source 12 in-line with an IR absorbing filter 14 and having an IR waveguide 18 directing the IR radiation from the IR source 12 onto the IR absorbing filter 14. The IR source, the IR absorbing filter, and the waveguide, can include any of those described herein.

FIG. 1.1E illustrates an embodiment of an IR filter system 10e that includes an IR source 12 in a non-on-line position relative to an IR absorbing filter 14 and having an IR waveguide 18 directing the IR radiation from the IR source 12 onto the IR absorbing filter 14. The IR source, the IR absorbing filter, and the waveguide, can include any of those described herein.

Embodiments of the present disclosure are capable of degrading a single contaminant or multiple contaminants in an environment. The term "environment" as used herein refers to those in the gas phase. In an embodiment, the environment is a HVAC system or a stand-alone filter system.

In an embodiment, one or more of the types of contaminant can include a biological contaminant and/or a chemical contaminant such as those described herein. In embodiments where it is desired to degrade a chemical contaminant, the temperature of the IR filter system may need to be raised higher and/or for a longer time frame than if only a biological contaminant is to be degraded. As described herein, embodiments of the present disclosure are capable of reaching temperatures that can degrade chemical contaminants and can hold those temperatures for a time period so that the chemical contaminant is degraded.

In an embodiment, the contaminant can include microorganisms such as bacteria, fungi, protozoans, algae, spores of any of these, endospores of any of these, cysts of any of these, and the like.

In addition, contaminants can include volatile organic compounds (VOCs), chemical warfare agents, and also include the following: aldehydes, aliphatic nitrogen compounds, sulfur compounds, aliphatic oxygenated compounds, halogenated compounds, organophosphate compounds, phosphonothionate compounds, phosphorothionate compounds, arsenic compounds, chloroethyl compounds, phosgene, cyanic compounds, or combinations thereof. In one embodiment, the contaminant is acetaldehyde, methyl mercaptan, ammonia, hydrogen sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, or combinations thereof. In an embodiment, the IR filter system can be heated to temperatures to degrade these chemical contaminants.

EXAMPLES

Now having described the embodiments of the present disclosure, in general, example 1 describes some additional embodiments of the present disclosure. While embodiments of the present disclosure are described in connection with example 1 and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Introduction

The disinfection of airborne pathogens has been given more attention due to the 2009 H1N1 swine flu pandemic[1] and the increasing threat of bioterrorism[2]. Pathogenic bioaerosols are a danger to humans and can be generated from a variety of sources; bioterrorism, occupational and agricultural processes, even coughing and sneezing aerosolize pathogens which can remain suspended and infectious for days. While there are a number of current bioaerosol control technologies including Ultraviolet Germicidal Irradiation (UVGI), antimicrobial filters, and photocatalytic oxidation, they have some noticeable weaknesses. The current technologies not only suffer from being expensive to install and maintain, but also are ineffective against highly resistant bacterial endospores (e.g., anthrax spores[3]).

Filtration is one of the most commonly used methods for the removal of particles, viable and nonviable alike[4]. High Efficiency Particulate Air (HEPA) filters, by definition, have 99.97% removal efficiency of 0.3-μm size particles. Nevertheless, sustained viability of microorganisms collected on the filters and reaerosolization are major concerns[5-9]. In addition to Heating Ventilation and Air Conditioning (HVAC) filters, personal respiratory filters loaded with pathogens also present a health and safety concern. In case of pandemic, the lack of personal respiratory filters may require contaminated filters to be reused. Therefore, it is critically important to effectively inactivate pathogens collected on a variety of fibrous filter media.

Using infrared (IR) radiation to flash heat the filter and inactivate pathogens can accomplish this task. In this research, a novel IR disinfection device for biologically contaminated air filtration media was developed. The device has the potential to be more effective in inactivating airborne pathogens than current air disinfection technologies while being more practical and cost effective as well.

Filters are effective in the collection of bioaerosols but alone do not exhibit an inhibitory effect on the growth of microbes[5]. Microbes can remain viable on a filter, multiply and reaerosolize after collection. Reaerosolization of a small fraction of collected bioaerosols may not seem significant; however, considering the infectious dose of some pathogens being very low (e.g., 25 cells for bioterrorism agent *Francisella tularensis*[10]), it can be hazardous for the people intended for protection. Without treatment, some microbes can survive on filters for weeks[6] and remain viable under environmental stress[9]. Hence, the filter must be disinfected.

As bacterial endospores are considered the most resistant microbes, the filter disinfection method will focus on inactivating endospores. If spores can be inactivated, it can be safety assumed that other microbes can be inactivated as well. Of the sterilization methods that will kill highly resistant spores, Ultra-High Temperature (UHT) treatment is among the most effective[11,12]. It is a sterilization method where a microorganism suspension is heated to a temperature of at least 135° C. for a few seconds. Martin et al. (1966) reported 4 log (99.99%) inactivation of spores in as little as 1 s in milk[11]. UHT treatment is used in the food industry to quickly sterilize spores in food products. Conduction/convection heating is commonly used but the proposed research will use IR radiation as the energy transfer mechanism. Due to its shallow penetration, IR radiation has the ability to generate an UHT quickly especially in thin materials like air filters.

Although UHT processes generally apply to sterilization of liquid medium, the concept can be applied to the disinfection of air filter media. The UHT IR disinfection device was developed by taking advantage of the properties of IR radiation and the physical characteristics of air filters. A commercial IR lamp was adopted to rapidly achieve UHT in an air filter to inactivate collected bioaerosols. The results presented here are static on-filter inactivation but future work will incorporate the device in an in-situ filtration system.

Materials and Methods

IR Radiation Heating Device

A commercially available 250 W IR heat lamp (BR40, Sylvania, MA) was used in this study because it is inexpensive, ubiquitous, as well as practical. For this particular lamp, IR radiation was emitted from the tungsten filament at 3000 K. Given the temperature of the filament, the wavelength of maximum energy output is approximated by Wien's displacement law in (1).

$$\lambda_{max} = \frac{b}{T} \qquad (1)$$

Where $\lambda_{max}$ is the wavelength of maximum energy output, T is the temperature of the filament, and b is Wein's proportionality constant equal to $2.898 \times 10^{-3}$ m K. The graph relating radiant power to wavelength is displayed in FIG. 2.1. It can be seen that most of the power emitted from the filament had a wavelength of approximately 1 μm.

It was observed from preliminary IR heating experiments that most glass fiber filters do not have significant IR absorption around 1 pm and consequently heated slowly. To rapidly achieve the UHT, an IR absorptive fiber mat was placed in contact with the filter to receive incoming radiation. Activated carbon, which is a chemical adsorbent with high absorption of short wave IR radiation and low specific heat capacity, was selected. Low pressure drop activated carbon fiber mats (Model ACC-5092-20, American Kynol, NY), were positioned on both sides of the filter forming a sandwich. A fiber mat was placed behind the filter to ensure that any transmitted or reflected radiation was absorbed. As the sandwiching fiber mats are less than 1 mm thick and as fibrous filters are equally thin, heat transfer across the filter occurred quickly. The filters were therefore primarily heated by conduction from the sandwich rather than heated directly by radiation.

The filament of the bulb was positioned 20 cm from the filter surface. To direct radiation toward the filter, a cylindrical aluminum foil waveguide was fitted around the lamp. Although not entirely IR reflective, the waveguide ensured that most of the radiation from the lamp reached the filter. By adding this waveguide, a significant temperature increase of the filter was observed compared to filter heating without the waveguide. Finally, aluminum foil was placed behind the sandwich to prevent any radiation transmitted through the filter from exiting the waveguide enclosure.

High Efficiency Particulate Air (HEPA) Filter

Selecting an appropriate HEPA filter was crucial for this research. The filter must be able to withstand intermittent heating to an UHT without decrease in filtration efficiency. Glass microfiber LydAir®MG (HEPA grade 4450HS, Lydall, NH) filters were chosen for their high efficiency and high temperature resistance. These filters maintain their efficiency for continuous operating temperature up to 480° C.

Temperature Measurement of Fiber Mat Heating by IR Radiation

To ensure precise and consistent radiation applications, the IR lamp was attached to a timer (Model 451, GraLab, OH) with accuracy of ±0.1% at 1 s. The temperature was measured with a calibrated infrared pyrometer (HHM290, Omega, CT). A special setup was constructed to obtain real-time temperature measurements of the filter during the heating process. First, a 37-mm diameter hole was cut in the aluminum foil behind the filter sandwich. The pyrometer detector was then placed 22 cm away and at a 40° angle to the exposed filter/fiber mat surface normal. Given the 22 cm distance, the detector field of view (25-mm spot) included the entire fiber mat. Measuring the temperature in this manner provided accurate temperature readings as only radiation emitted from the filter/fiber mat entered the detector.

To make the best estimation of the actual filter temperature, two sets of temperature measurements were taken. In the first set, the temperature of a single fiber mat was measured. Because the pyrometer detected the temperature at the bottom of the fiber mat, the recorded temperature represented the temperature at the top of the filter when placed in the sandwich. In the second set, an identical measurement setup was employed but now the temperature of a half-sandwich (a fiber mat top and filter bottom) was measured so that the filter was in the field of view of the pyrometer. The corresponding temperature represented the temperature at the bottom of the filter. The temperatures from the two sets were then averaged at each time. This averaged temperature is then the estimated temperature that the average microorganism experiences assuming bioaerosol collection is uniform.

Preparation of Test Bioaerosols

Three microorganisms, *Escherichia coli*, MS2 Bacteriophage and *Bacillus subtilis* endospores were tested, as benign surrogates representative of more dangerous microbes. As the test organisms resemble a wide range of bioaerosols, they provided an estimation of the inactivation of a variety of possible airborne pathogens.

*Escherichia coli*

*Escherichia coli* (*E. coli*), which is often selected as a test microorganism for germicidal tests for bioaerosols, was used in this study as a representative of bacterial vegetative cells. It is a Gram-negative rod-shaped bacterium with size of 0.8 μm×2 μm and aerodynamic diameter of 0.8 μm. *E. coli* was first inoculated on a Difco Nutrient Agar (Becton, Dickinson and Company, MD) plate from stock (ATCC number 15597). This plate was then incubated at 37° C. for 24 hours. Before each experiment, an *E. coli* colony from the plate was inoculated on a Difco Nutrient Agar slant and incubated for 24 hours. The *E. coli* population on the slant was then transferred to Ringer's solution (Fisher, Cat. No.: S77939, NY) by vortexing. This suspension was then used in aerosolization[13].

MS2 Virus Bacteriophage

As a second test bioaerosol, MS2 virus bacteriophage (*E. coli* bacteriophage, MS2; ATCC® 15597-B1) was selected as it is a surrogate of human pathogen entrovirus due to similarities in structure and resistance. MS2 is an un-enveloped, icosahedral-shaped virus that is 27.5 nm in diameter. Freeze-dried MS2 was aerosolized with DI water and propagated in *E. coli* (ATCC number 15597) for culturing[14].

*Bacillus subtilis* endospores

*Bacillus subtilis* endospores were tested as a representative of bacterial endospores. A Gram-positive bacterium, *B. subtilis* has the ability to sporulate and has been used extensively as a surrogate to *Bacillus anthracis* spores. *B. subtilis* endospores are ellipsoidal in shape, approximately 0.8-1.2 μm in length, and have an aerodynamic diameter of 0.9 μm.

*B. subtilis* vegetative cells were obtained from the University of Florida Department of Microbiology and Cell Sciences. The vegetative cells were subject to the process outlined by Lee et al. (2008) to induce sporulation[15]. African violet agar, which included 200 mL African violet soil extract, 800 mL DI water, 1 g yeast extract (Fisher Scientific) and 15 g Difco Nutrient Agar was used. *B. subtilis* vegetative cells were inoculated in this agar and incubated at 37° C. for endospore development. After one week, a 2 mL DI water suspension of *B. subtilis* was created from the slant and heated in a water bath at 80° C. for 30 minutes to kill remaining vegetative cells. The suspension was subsequently cooled and centrifuged at 3,500 RPM for 10 minutes to remove cell debris. After applying the malachite green spore-staining technique, microscopic analysis showed the absence of vegetative cells in the purified suspension. The spore suspension was used immediately after the purification process.

Filter Loading and IR Flash Disinfection

Bioaerosol Filter Loading

To determine the effectiveness of the IR radiation disinfection device, filters were first loaded with test microbes to simulate the collection of bioaerosols by a fibrous filter.

A Collison nebulizer with 40 mL of microorganism suspension operating at 15 LPM was used to aerosolize the three test microbes using particle-free compressed air. The flow was directed to the dilution dryer where water content evaporated yielding the microorganism aerosol. The flow then split into three parallel flows toward the HEPA filters. Three filters were loaded at a time to obtain triplicate data. The filters were loaded for 45 minutes at a face velocity of 10 cm/s. After loading, the filters were removed from the flow and subjected to the IR disinfection device.

IR Flash Disinfection

Once removed from the filter holder, a loaded filter was cut into four equal quadrants. One quadrant, the control, was directly suspended in 20 mL of Ringer's solution (*E. coli*) or 20 mL of DI water (MS2 and *B. subtilis*) and vortexed for 2 minutes to extract the microorganisms from the filter fibers. A sample was taken from this vortexed solution, serially diluted, plated with required growth medium, and incubated at the optimal growth temperature for 24 hours. The remaining three quadrants were irradiated with the IR disinfection device for 1, 3, and 5 s for each test microbe. At least three replicates were conducted for each time application. The irradiated filter quadrants were then cultured by the process described with the control. After incubation, the number of Colony Forming Units (CFU) or Plaque Forming Units (PFU) were counted for the control and experimental plates. The microbe survival, S, was calculated by (2), $$S = \frac{CFU_{experimental}}{CFU_{control}} \qquad (2)$$

where CFU represents the number of colony (or plaque for MS2) forming units counted from the control and experimental samples at appropriate dilutions. Log inactivation, defined by (3), was used as the metric of inactivation in this study.

$$\log \text{inactivation} = -10 \, g(S) \qquad (3)$$

To ensure that the 4 quadrants collected similar amounts of bioaerosols during the loading process, a triplicate set of *B. subtilis* tests, where all 4 quadrants were not irradiated, was conducted. Although a 20-50% coefficient of variation was found, statistical analysis indicated that observed inactivation from irradiation was statistically different from apparent inactivation due to loading inconsistencies.

Results

Temperature Measurements

Temperature measurements of the activated carbon fiber mat after IR irradiation are displayed in FIG. 2.4. The filter was able to achieve the UHT of 135° C., which is required for flash sterilization, within 2 s from room temperature. Furthermore, the filter was able to reach a maximum steady state temperature of about 360° C. (FIG. 2.4), which not only demonstrates the ability of the device to achieve the UHT within seconds but also its potential to reach the temperatures needed for chemical decomposition/desorption processes. The rapid heating of the activated carbon fiber mat is a result of the shallow penetration of IR radiation. For absorptive materials, IR penetrates only micrometers to millimeters so all the emitted energy is absorbed within a thin surface layer[16]. This physical property of IR radiation is ideal for heating a thin fiber mat/filter. IR heating is also especially effective for targets with large area exposed to incident radiation. In addition, fiber mats have a large surface area to mass ratio, causing the fiber mat to heat very quickly with the received energy. During heating tests, it was noticed that the fiber mats cooled very quickly. Again, due to the fiber mat's relatively large surface area, it was able to dissipate heat quickly to the surrounding environment. This rapid cooling spares the fiber mat/filter from accidental heat damage.

IR Disinfection of Collected Bioaerosols on the Filter

The inactivation data are presented in FIG. 2.5 as log inactivation. Log inactivation provides an understanding of the order of magnitude of microorganism inactivation on a logarithmic scale, where 1 log is 90% inactivation, 2 logs is 99% inactivation, 3 logs is 99.9% inactivation, etc. The error bars represent 1 standard error from the mean log inactivation value.

It can be seen from FIG. 2.5 that significant microbe inactivation was achieved with short time applications. An IR application of just 3 s from the device resulted in approximately 5 log inactivation (99.999%) of MS2 virus on the filter. Similar to MS2 virus, about 4 log inactivation of *E. coli* was achieved within 3 s of IR application. The more heat resistant *B. subtilis* spores, however, required 5 seconds of irradiation for greater than 3 log inactivation. This was expected due to the spore coat and the presence of dipicolinic acid and calcium in the cell protecting the inner proteins against denaturation[17]. Regardless of this observation, the spores, which tend to be extremely resistant to many disinfection processes, were inactivated relatively easily by the IR device.

DISCUSSION

Flattening in the Log Inactivation Curve with Longer Applications

Although the data in FIG. 2.5 displays significant on-filter microbe inactivation, the values do appear to approach a limit at increasing times. This trend is attributed to relatively low control number of CFU/PFU. Control CFU/PFU values were approximately $10^5$ per mL in the vortexed sample, providing the ability to detect at most 5 log inactivation. If the filters were loaded to a higher concentration, greater log inactivation may have been observed. However, a similar control concentration was also reported in other filter disinfection studies[18].

Another explanation for flattening in the inactivation curve is that the device is sufficiently effective to completely disinfect *E. coli* and MS2 virus within 3 s. Nearly identical inactivation values were seen regardless of increasing time application. Given a control filter CFU, if no colonies are observed on both experimental 3 and 5 s plates, the log inactivation will be identical by Equation 3 and cause flattening of the curve with increasing time. The inactivation values at these time applications are simply conservative estimates to the actual inactivation. If this is the case, practical use with the IR device would not require greater than 3 s for filter disinfection of these heat sensitive microbes.

Device Effectiveness

There are several explanations why the IR filter disinfection device was so effective. First, although dry heat disinfection was performed in this study, it is important to recall the energy transfer mechanisms involved. Dry heat is less effective than moist heat because moisture is better in the convective energy transfer toward a target surface (e.g., autoclave)[17]. However, the energy transfer mechanisms for this device are radiation and conduction rather than convection. IR radiation does not require a heat transfer medium so this allows for the device to be effective without the presence of moisture. Second, the well established protocol for dry heat sterilization (160° C. for 120 min) only applies to objects that are sufficiently thick where deep heat penetration is required. Because an air filter is thin, conduction heating from the sandwich is adequate for essentially a surface sterilization process. An alternative explanation for the effectiveness of the device may be the non-thermal effects of the IR radiation. Because IR radiation has a wavelength between ultraviolet and microwaves, non-thermal injury or inactivation of the microbes can occur. Although the radiation was expected to be absorbed by the activated carbon fiber mat, transmitted radiation may have this additional non-thermal effect on collected microbes.

In general, the results of this work compare somewhat to scientific studies with respect to IR inactivation kinetics. A dry heat IR inactivation study with *B. subtilis* spores by Molin and Ostlund (1975) found a D-value (the time required for 1 log inactivation) of 3.2 s at 180° C.[19]. In contrast, Hamanaka et al. (2006) found IR inactivation much more challenging with a D-value of minutes although temperature was not carefully monitored (but greater than 100° C.)[29]. In that study, increasing the IR absorption of medium in contact with the spores was not attempted. In the present study, however, highly absorptive activated carbon fiber mats in contact with a contaminated filter were irradiated resulting in much greater inactivation.

CONCLUSIONS

The presented device was extremely effective, inactivating up to 5-log of test microorganisms within seconds. Compared to current filter disinfection technologies, like ultraviolet radiation[21], microwave radiation[22], and biocidal filters[19], the IR device requires shorter application times while achieving orders of magnitude greater inactivation. It also outperformed newer and relatively complicated approaches like silver nanoparticles[23] and photocatalytic oxidation[24]. Furthermore, these technologies are limited by their strong dependence on environmental conditions and microbe species, which is not the case here.

If incorporated into an in-situ filtration system, the presented IR device has the potential to be a significant improvement to current bioaerosol control technologies. HEPA filtration with immediate UHT treatment will result in filtration and inactivation of greater than 99% of all bioaerosols. A future in-situ system would have the ability to effectively remove spore aerosols from the air stream, a task which has not been accomplished with any current practical technology High temperature resistant filters were used in this study but were not necessarily required. If only vegetative cells and viruses were targeted, standard commercial filters could have been substituted instead. Standard glass fiber filters can easily withstand intermittent heating to temperatures required for bacteria and virus inactivation for a few seconds The filter sandwich system offers the disinfection device great adaptability. Because of the activated carbon sandwich, different filters can be substituted without concern about efficient radiative transfer. Given that the activated carbon fiber mat has negligible pressure drop (21 Pa, at face velocity of 5.3 cm/s), the device can be easily incorporated into existing systems without significantly increasing costs. In addition to biological applications, the use of activated carbon fiber mats provides the ability for the adsorption/IR decomposition of chemical agents.

The IR device also demonstrates significant promise in the disinfection of personal respiratory filters. Again, if only virus or bacterial vegetative cells are targeted, the filters can be flash irradiated with the device (not necessarily to an UHT) resulting in quick and effective disinfection. Because only heat sensitive microbes would be targeted, the filters would not incur heating damage. In only a few seconds, contaminated respiratory filters would be ready for reuse. During pandemic situations, the ability to decontaminate personal filters this quickly would be invaluable.

Overall, the IR device is inexpensive (less than $5), simple, quick, and extremely effective in disinfecting contaminated filter media. Unlike UVGI, the present device is only required to be on for a few seconds making it extremely cost-effective. Because of these features, it has uses in military, commercial, and even life science research applications. Biosafety cabinets, for example, which use a HEPA filter to remove biological contaminants and protect researchers, are used in science labs across the world. The described IR disinfection device could be installed in these cabinets to provide a safer working environment with less contamination.

References for Example 1, Each of which are Incorporated Herein by Reference

1. Fraser, C., Donnelly, C., Cauchemez, S., Hanage, W., Van Kerkhove, M., Hollingsworth, T., Griffin, J., Baggaley, R., Jenkins, H., Lyons, E., Jombart, T., Hinsley, W., Grassly, N., Balloux, F., Ghani, A., Ferguson, N., Rambaut, A., Pybus, O., Lopez-Gatell, H., Alpuche-Aranda, C., Chapela, I., Zavala, E., Guevara, D., Checchi, F., Garcia, E., Hugonnet, S., Roth, C. and The WHO Rapid Pandemic Assessment Collaboration. (2009) Pandemic potential of a strain of influenza A (H1N1): early findings. *Science* 324, 1557-1561.
2. Henderson, D. (2004) The threat of aerosolized biological weapons. *ASHRAE J* 46, 50-53.
3. Nicholson, W., Munakata, N., Horneck, G., Melosh, H. and Setlow, P. (2000) Resistance of *Bacillus* endospores to extreme terrestrial and extraterrestrial environments. *Microbiol Mol Biol Rev* 64, 548-572.
4. Hinds, W. C. (1999) *Filtration. In Aerosol Technology.* 2nd edn. pp. 182-205. New York, N.Y.: John Wiley & Sons, Inc.
5. Maus, R., Goppelsröder, A. and Umhauer, H. (1997) Viability of bacteria in unused air filter media. *Atmos Environ* 31, 2305-2310.
6. Wang, Z. (1999) Survival of bacteria on respirator filters. *Aerosol Sci Technol* 30, 300-308.
7. Möritz, M., Peters, H., Nipko, B. and Widen, H. (2001) Capability of air filters to retain airborne bacteria and molds in heating, ventilating and air-conditioning (HVAC) systems. *Int J Hyg Environ Health* 203, 401-409.
8. Jankowska, E., Reponen, T., Willeke, K., Grinshpun, S. A. and Choi, K. J. (2000) Collection of fungal spores on air filters and spore reentrainment from filters into air. *J Aerosol Sci* 31, 969-978.
9. Maus, R., Goppelsröder, A. and Umhauer, H. (2001) Survival of bacterial and mold spores in air filter media. *Atmos Environ* 35, 105-113.
10. McCrumb, F. (1961) Aerosol infection of man with *Pasteurella tularensis*. *Bacteriol Rev* 25, 262-267.
11. Martin, J. H., Harper, W. J. and Gould, I. A. (1966) Ultra-high temperature effects on selected *Bacillus* species. *J. Dairy Sci* 49, 1367-1370.
12. Edwards, J. L., Busta, F. F. and Speck, M. L. (1965) Thermal inactivation characteristics of *Bacillus subtilis* spores at ultrahigh temperatures. *Appl Environ Microbiol* 13, 851-857.
13. Ratnesar-Shumate, S., Wu, C. Y., Wander, J., Lundgren, D., Farrah, S., Lee, J., Wanakule, P., Blackburn, M. and Lan, M. (2008) Evaluation of physical capture efficiency and disinfection capability of an iodinated biocidal filter medium. *Aerosol Air Qual Res* 8, 1-18.
14. Lee, J. H., Wu, C. Y., Lee, C. N., Anwar, D., Wysocki, K. M., Lundgren D. A., Farrah, S., Wander, J., and Heimbuch, B. K. (2009) Assessment of iodine-treated filter media for removal of and inactivation of MS2 bacteriophage aerosols. *J Appl Microbiol* 107, 1912-1923.
15. Lee, J. H., Wu, C. Y., Wysocki, K. M., Farrah, S. and Wander, J. (2008) Efficacy of iodine-treated biocidal filter media against bacterial spore aerosols. *J Appl Microbiol* 105, 1318-1326.
16. Wade, P. (1987) Biscuit baking by near-infrared radiation. *J Food Eng* 6, 165-175.
17. McDonnell, G. E. (2007) *Physical Sterilization. In Antisepsis, disinfection, and sterilization.* pp. 165-190. Washington D.C: ASM Press.
18. Rengasamy, S., Fisher, E. and Shaffer, R. (2010) Evaluation of the survivability of MS2 viral aerosols deposited on filtering face piece respirator samples incorporating antimicrobial technologies. *Am J Infect Control* 38, 9-17.
19. Molin, G. and Östlund, K. (1975) Dry-heat inactivation of *Bacillus subtilis* spores by means of infra-red heating. *Antonie Van Leeuwenhoek* 41, 329-335.
20. Hamanaka, D., Uchino, T., Furuse, N., Han, W. and Tanaka, S. (2006) Effect of the wavelength of infrared heaters on the inactivation of bacterial spores at various water activities. *Int J Food Microbiol* 108, 281-285.
21. Kujundzic, E., Matalkah, F., Howard, C., Hernandez, M. and Miller, S. (2006) UV air cleaners and upper-room air ultraviolet germicidal irradiation for controlling airborne bacteria and fungal spores. *J Occup Environ Hyg* 3, 536-546.
22. Zhang, Q., Damit, B., Welch, J., Park, H., Wu, C. Y. and Sigmond, W. (2010) Microwave assisted nanofibrous air filtration for disinfection of bioaerosols. *J Aerosol Sci* 41, 880-888.
23. Lee, B., Yun, S., Jung, J. and Bae, G. (2010) Effect of relative humidity and variation of particle number size distribution on the inactivation effectiveness of airborne silver nanoparticles against bacteria bioaerosols deposited on a filter. *J Aerosol Sci* 41, 447-456.
24. Chuaybamroong, P., Chotigawin, R., Supothina S., Sribenjalux P., Larpkiattaworn S., and Wu C. Y. (2010) Efficacy of photocatalytic HEPA filter on microorganism removal. *Indoor Air* 20, 246-254.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of degrading contaminates, comprising:
providing an IR filter system;
trapping contaminants in the IR absorbing filter;
irradiating the IR absorbing filter with IR radiation, wherein the IR absorbing filter absorbs IR radiation causing the IR absorbing filter to increase in temperature to about 135° C. or greater; and
degrading substantially all of the contaminants trapped in the IR absorbing filter,
wherein the IR filter system includes:
an IR source; and
an IR absorbing porous filter positioned within the air intake to filter air passing through the air intake, where the IR source is positioned relative to the IR absorbing porous filter so that IR radiation from the IR source is directed onto the IR absorbing porous filter to cause the IR absorbing porous filter to increase in temperature to about 135° C. or greater.

2. The method of claim 1, wherein the irradiating causes the temperature to increase to about 350° C. or greater in less than 5 seconds.

3. The method of claim 1, wherein a wavelength of the IR radiation is selected to specifically degrade a contaminant.

4. A method of degrading contaminates, comprising:
providing an IR filter system;
trapping contaminants in the filter;
irradiating the IR absorbing structure with the IR radiation source, wherein the IR absorbing structure absorbs IR radiation causing the IR absorbing structure to increase in temperature to about 135° C. or greater, wherein the filter increases in temperature since it is in contact with the IR absorbing structure; and
degrading substantially all of the contaminants trapped in the IR absorbing filter,
wherein the IR filter system includes:
an IR source;
a particulate matter filter; and
an IR absorbing structure, wherein the particulate matter filter and the IR absorbing structure are disposed in a plane parallel each other, wherein the particulate matter filter and the IR absorbing structure are in contact with each other along one side, wherein the IR source is positioned relative to the IR absorbing structure and the particulate matter filter so that IR radiation from the IR source is directed onto the IR absorbing structure to cause the IR absorbing structure and the particulate matter filter to increase in temperature to about 135° C. or greater.

5. The method of claim 4, wherein the IR irradiation causes the temperature to increase to about 135° C. or greater in less than 5 seconds.

6. The method of claim 4, wherein the irradiating causes the temperature to increase to about 350° C. or greater in less than 5 seconds.

7. The method of claim 4, wherein a wavelength of the IR radiation is selected to specifically degrade a contaminant.

* * * * *